(12) United States Patent
Haas

(10) Patent No.: US 8,823,945 B2
(45) Date of Patent: Sep. 2, 2014

(54) MEASURING DEVICE FOR DETERMINING A VEGETATION INDEX VALUE OF PLANTS

(75) Inventor: Tobias Haas, Bad Heilbrunn (DE)

(73) Assignee: Georg Fritzmeier GmbH & Co. KG, Grobhelfendorf (DE)

( * ) Notice: Subject to any disclaimer, the term of this patent is extended or adjusted under 35 U.S.C. 154(b) by 273 days.

(21) Appl. No.: 13/388,973

(22) PCT Filed: Aug. 4, 2010

(86) PCT No.: PCT/EP2010/061337
§ 371 (c)(1),
(2), (4) Date: Dec. 20, 2012

(87) PCT Pub. No.: WO2011/015598
PCT Pub. Date: Feb. 10, 2011

(65) Prior Publication Data
US 2013/0120753 A1    May 16, 2013

(30) Foreign Application Priority Data

Aug. 5, 2009  (DE) .......................... 10 2009 036 148
Nov. 6, 2009  (DE) .......................... 10 2009 052 159

(51) Int. Cl.
*G01N 21/55*   (2014.01)

(52) U.S. Cl.
USPC .......................................... 356/448; 356/445

(58) Field of Classification Search
USPC .................................. 356/448, 445, 317–327
See application file for complete search history.

(56) References Cited

U.S. PATENT DOCUMENTS 3,910,701 A    10/1975    Henderson et al.
6,246,471 B1    6/2001    Jung et al.
(Continued)

FOREIGN PATENT DOCUMENTS

AU             199668536          8/1996
DE       10 2007 017 482         11/2007
(Continued)

OTHER PUBLICATIONS

Optoelectronic Sensors in Medical Applications, Ray King, Texas Advanced Optoelectronic Solutions (TAOS), Inc.; XP-002601924; Sensors, Sep. 2003.
(Continued)

*Primary Examiner* — Tri T Ton
(74) *Attorney, Agent, or Firm* — O'Melveny & Myers LLP

(57) ABSTRACT

The invention relates to a measuring device for determining a vegetation index value (REIP) of plants. The measuring device comprises a plurality of light emitting elements, each of which emits substantially monochromatic light at a predetermined wavelength, a light receiving element which receives light from the light emitting elements reflected by the plants and generates a signal indicating the respective intensity of the received light, and a control means which successively activates the light emitting elements in a cyclical sequence, determines the respective intensity of the reflected light based on the output signal of the light receiving element, and calculates the vegetation index value based on the determined intensities of the overall measurement cycle. According to the invention, a light frequency converter is provided as the light receiving element.

8 Claims, 4 Drawing Sheets

(56) References Cited

U.S. PATENT DOCUMENTS

| | | |
|---|---|---|
| 6,635,859 B2 | 10/2003 | Wiles, Jr. |
| 7,408,145 B2 | 8/2008 | Holland |
| 8,358,420 B1 * | 1/2013 | DeWitt et al. ............ 356/452 |
| 2004/0076325 A1 | 4/2004 | Wada et al. |
| 2005/0275052 A1 | 12/2005 | Raynor |
| 2006/0132780 A1 | 6/2006 | Holland et al. |
| 2006/0208171 A1 | 9/2006 | Holland |
| 2008/0291455 A1 | 11/2008 | Holland |

FOREIGN PATENT DOCUMENTS

| | | |
|---|---|---|
| JP | 06-003187 | 1/1994 |
| JP | 09-257577 | 10/1997 |
| JP | 2007/501410 | 1/2007 |
| WO | 02/039094 | 5/2002 |

OTHER PUBLICATIONS

Shaping the Future of Light Sensing Solutions, TAOS Texas Advanced Optoelectronic Solutions; XP-002601925.

Estimating the Nitrogen Nutrition Index Using Spectral Canopy Reflectance Measurements, Mistele B et al: European Journal of Agronomy, Elsevier, BD. 29, NR. 4, Nov. 1, 2008, Seiten 184-190, XP025467121, ISSN: 1161-0301, DOI:10.1016/J.EJA.2008.05.007.

TSL220; Light-To-Frequency Converter, Texas Instruments; SOES003-Aug. 1990—Revised Jun. 1991; pp. 1-9; Addendum p. 1 (Package Option Addendum Apr. 8, 2005); Mechanical Data (1 Page); Important Notice Page (1 Page).

* cited by examiner

Reflection spectra of winter wheat

MEASURING DEVICE FOR DETERMINING A VEGETATION INDEX VALUE OF PLANTS

FIELD OF INVENTION

The present invention relates to a measuring device for determining a vegetation index value (REIP) of plants in accordance with the preamble of claim 1.

BACKGROUND INFORMATION

A known measuring device can be seen in US 2006/0208171 A1. This measuring device serves to determine a vegetation index value of plants; in particular this known measuring device is intended to determine the so-called REIP ("Red Edge Inflection Point") vegetation index. Plant measurements of this type have the purpose of enabling the utilization of the obtained measurement quantities for a determination of the most important characteristic values of the plant, namely, in the case of the REIP vegetation index mainly for determining the current nitrogen content of the plants being measured; based on the determined nitrogen content it is then possible to draw up a suitable fertilization plan for the field in question; in practice, e.g., corresponding GPS-supported fertilization systems are already being used which employ the determined nitrogen values to optimally supply fertilizer to specific surface areas.

The known vegetation index measurements are based on the light absorption or reflection characteristics of plants as shown in FIG. 3: According to this, the plants possess the general property of absorbing light of certain wavelengths (namely, <700 nm) while reflecting light of longer wavelengths (i.e. >800 nm). As may be seen from FIG. 3, the blue, green and red light components are absorbed by the leaves of the plant, with the cell structure and the water content of the plant causing a shift from absorption to reflection along a steep flank ("red edge") in the beginning infrared range.

Investigations have shown that this transitional area of the red edge ("Red Edge Inflection Point"—REIP) may be utilized for determining the chlorophyll content and the nitrogen content of plants. Namely, there exists the interrelation between the plant's REIP and its nitrogen content as shown in FIG. 4, and it could be demonstrated by Guyot and Baret (1988) that four measurements each with different wavelengths are sufficient for determining the nitrogen content.

In document US 2006/0208171 A1 mentioned at the outset it is therefore proposed to provide four light-emitting elements having the form of light-emitting diodes (LEDs) for the measurement of the REIP value and thus of the nitrogen content, each of which emits substantially monochromatic light of a predetermined wavelength within the REIP range (i.e., in the range between 660 and 780 nm); a control means successively controls these four light-emitting diodes in a cyclical sequence, with the respective intensity of the reflected light being determined based on the output signal of a light sensor element, and the currently valid vegetation index value or REIP value lastly being calculated based on the determined intensities of the overall measuring cycle.

In this known measurement device the light sensor element used is a photodiode whose analog and moreover highly noisy output signal must be subjected to complex processing (phase detection) and must then furthermore be subjected to an A/D conversion for the further calculation. Studies have shown that this strongly affects the attainable measurement accuracy; in addition the hardware expenditure is comparatively high on account of the additionally required phase detector and A/D converter.

SUMMARY OF THE INVENTION

The invention is based on the object of further developing a measuring device for determining a vegetation index value or REIP value of plants in accordance with the preamble of claim 1 so as to allow a reduction of the hardware expenditure despite an enhanced measurement accuracy.

In accordance with the invention, this object is achieved through the disposition specified in the characterizing portion of claim 1.

The invention thus proposes to provide a light frequency converter as a light receiving element. A like light frequency converter exhibits very low internal noise, with the measurement accuracy being correspondingly high. In order to determine the light intensity it is moreover sufficient to determine the time interval between the flanks of the output frequency of the converter, which can be achieved with any kind of microcontroller in the absence of additional components. The expenditure in terms of hardware is thus limited to the comparatively low-cost light frequency converter, with the complexity in terms of circuitry thus being very low in accordance with the invention.

In accordance with the advantageous development of the invention specified in claim 2 there is furthermore provided a current regulating means (LED-C) which controls the current supplied to each light emitting element and which was calibrated (at the manufacturer's) such that at a defined distance from a defined white surface, each light emitting element generates the same output signal in the light frequency converter.

Studies have provided evidence that this makes it possible to fully compensate any fluctuations of the ambient light. Complex compensation of the ambient light as proposed, e.g., in U.S. Pat. No. 7,408,145 B2 may thus be omitted altogether. This serves to further reduce the manufacturing costs of the measuring device in accordance with the invention.

Further advantageous developments of the invention are subject matter of the further subclaims.

In the following, the invention shall be explained in more detail through the description of an embodiment while making reference to the drawings.

DETAILED DESCRIPTION

Figure 1:
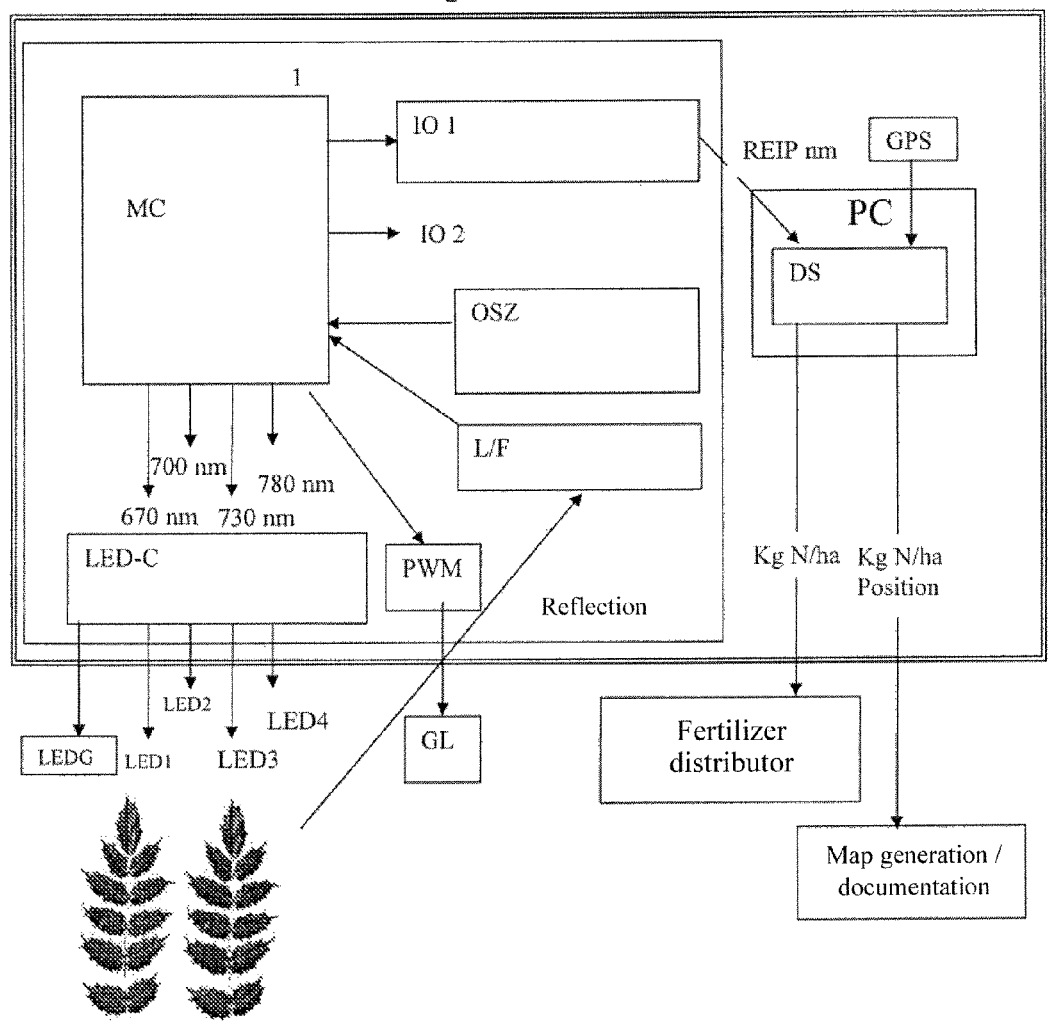
FIG. 1 is a block diagram of an embodiment of the invention.

In accordance with FIG. 1, the measuring device schematically shown under 1 consists of a central control means MC which may for instance be a commercially available microcontroller, an oscillator or resonant circuit OSZ providing the time base (of 40 MHz in the practical example) required for the frequency measurement, a current regulation module LED-C for light-emitting diodes LED1 to LED4, and a light/frequency converter L/F which may for instance be of the type TSL 230 R. Apart from a general-purpose interface IO2 presently not defined in more detail, one or more interface IO1 is provided which is executed as a serial interface and generates a Bluetooth signal.

The four light-emitting diodes LED1 to LED2 generate light of respective different wavelengths, with light-emitting diode LED1 generating light of 670 nm, LED2 generating light of 700 nm, LED3 generating light of 740 nm, and LED4 generating light to of 780 nm; each one of these light-emitting diodes has a half-width of the emitted light between 20 and 30 nm. In order to preclude fluctuations of brightness caused by the supply voltage of these light-emitting diodes, the current supplied to them is controlled by means of transistors of the current regulation module LED-C. The current regulations of the individual light-emitting diodes are calibrated such that they each generate the same output frequency at a defined distance from a defined white surface in the light following the conversion in the light/frequency converter L/F. By means of this white balance it is made sure that both the standard dispersion of the light-emitting diodes and the spectral sensitivity of the light/frequency converter are compensated. The white balance moreover allows to do away with a measurement of the ambient light, for the ambient light is compensated by the vegetation index REIP and need not be measured and calculated.

In accordance with FIG. 1 there is furthermore provided a fifth light-emitting diode LEDG which emits green light (preferably having a wavelength of 585 nm). By means of this fifth light-emitting diode LEDG it is possible to obtain information about the biomass in the early stages of supply in which the ground is still visible. To this end the determined brightness value of the light-emitting diode LEDG is subtracted from the one of LED1 (670 nm). The smaller the determined difference, the more plants are situated below the sensor relative to the ground.

Lastly there is also an incandescent lamp GL which is driven by the control means MC via a pulse-width modulation circuit PWM. With the aid of this incandescent lamp it is possible to obtain correct measurement values even in twilight or during the night. This incandescent lamp GL is oriented so as to illuminate at least the one area at which the light-emitting diodes are directed.

The measuring device of the invention operates as follows: For the performance of one measuring cycle the central control means MC successively drives each one of the light-emitting diodes LED1 to LED4 for a predetermined time period, or period, via the current regulation module LED-C. The duration of this period is designed such that the light/frequency converter L/F will generate an output pulse.

Initially the light-emitting diode LED1 is turned on for the predetermined time period so that the plants shown schematically in FIG. 1 are illuminated with a wavelength of 670 nm; the light reflected by the plants is then received by the light/frequency converter L/F, and based on the time interval between the flanks of the output signal of the light/frequency converter L/F the central control means MC subsequently determines the light intensity P1 associated with the wavelength 670 nm, which is an indication of the degree of reflection at this wavelength. This determined light intensity P1 is then stored. Subsequently the light-emitting diodes LED2 to LED4 are equally each turned on for the predetermined time period in order to determine and store, based on the flanks of the associated output signal of the light/frequency converter L/F, the respective intensity values P2 to P4 for the wavelengths of 700 nm, 740 nm, and 780 nm.

After the completion of such a measuring cycle, all four measurement values for the light intensities P1 to P4 are then stored in the central control means MC; these values are substituted in the following formula:

$$REIP = \lambda_2 + (\lambda_3 - \lambda_2)((P_1 + P_4)/2 - P_2)/(P_3 - P_2)$$

wherein the values $P_1$ to $P_4$—as was explained in the foregoing—each express the measured intensity of the reflected light of the respective light-emitting diode LED1 to LED4 and $\lambda_1$, $\lambda_2$, $\lambda_3$ or $\lambda_4$ at their specific wavelengths (thus, the values 670, 700, 740, and 780 nm).

The calculated REIP value of this formula is a direct indication of the nitrogen content of the plant(s) irradiated by the light-emitting diodes in the respective measuring cycle.

In accordance with FIG. 1 a signal specifying the calculated value for the vegetation index REIP or, respectively, the corresponding nitrogen content is emitted via the interface 101. This signal is received by a computer PC which contains a fertilization system mapped by software; this fertilization system is capable of determining the quantity of nitrogen required per hectare of surface in order to enable, e.g., appropriate control of a fertilizer distributor. In addition the nitrogen quantity measured in the respective position may be determined by means of a GPS sensor for the purpose of carrying out a corresponding map generation or documentation.

The afore-described measuring cycle is repeated continuously after a complete run of all four light-emitting diodes and following calculation of the REIP value, so that depending on the moving velocity of the measuring device a nearly complete detection of the nitrogen content of all of the scanned plants is possible.

If the ambient brightness is insufficient due to twilight or due to night-time work, the control means MC drives the incandescent lamp GL via the pulse-width modulation circuit PWM such that its brightness is increased proportionally with increasing darkness.

Figure 5:
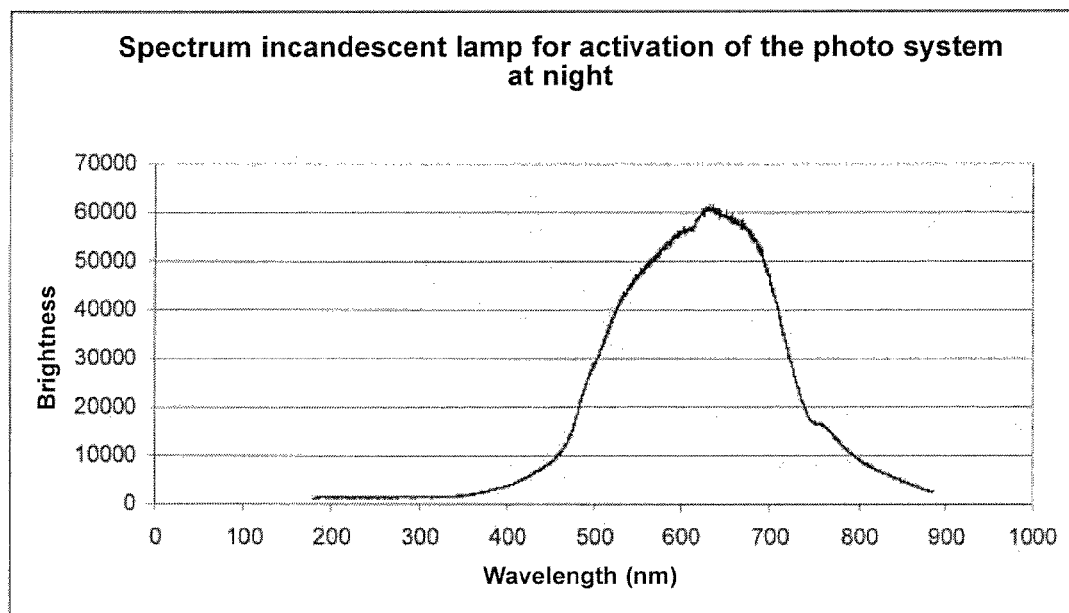
FIG. 5 shows the spectrum of a light bulb used at night for illuminating the plants.

The reason for the use of an incandescent lamp controlled in such a way is the following: As a general rule, plants have two photosystems operating independently of each other; one of these two photosystems operates in particular at 680 nm, while the other one operates at 700 nm. If, now, one were to sequentially irradiate the plants with monochromatic light only, these two photosystems would not operate optimally due to the so-called Emerson effect. Thus the absorption values would change correspondingly, with the REIF value calculated at darkness not conforming with the respective daylight values. In contrast, the incandescent lamp provided in accordance with the invention emits light having the spectral curve shown in FIG. 5, and thus encompasses a larger range of wavelengths. In other words, even in darkness the incandescent lamp GL irradiates both photosystems of the plants in such a way that their operation becomes optimum again. Thus it is possible even in darkness to retrieve the daylight measurement values. If the light frequency converter is not sufficiently illuminated by the ambient light any more, the control means MC controls the incandescent lamp GL via the pulse-width modulation circuit PWM in such a way that the light level will not drop below a minimum ambient light level. The incandescent lamp GL thus is turned off during the day, begins to shine faintly in twilight, and presents its full luminous power in darkness.

Figure 2:
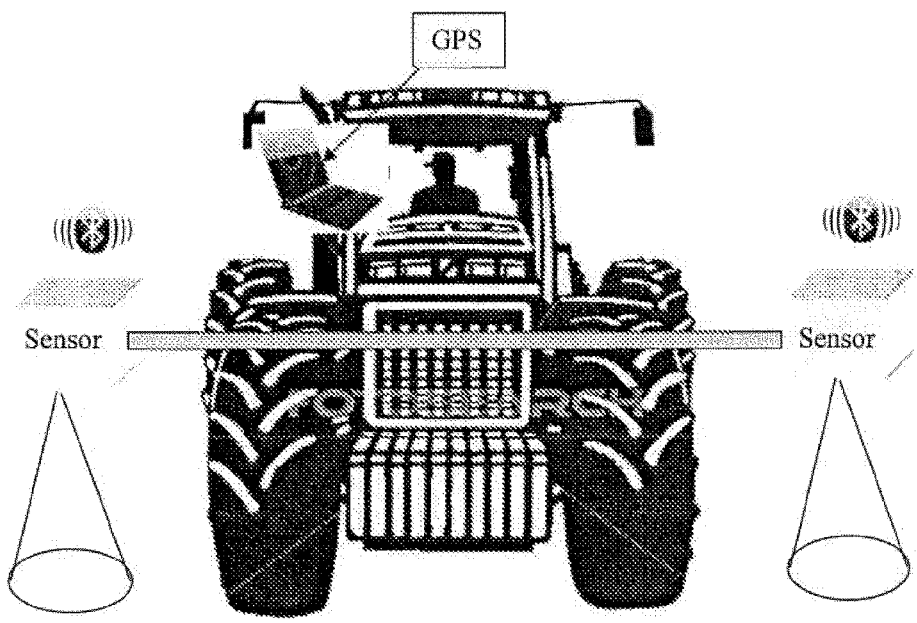
FIG. 2 is a schematic representation of a typical application of the invention.
Figure 3:
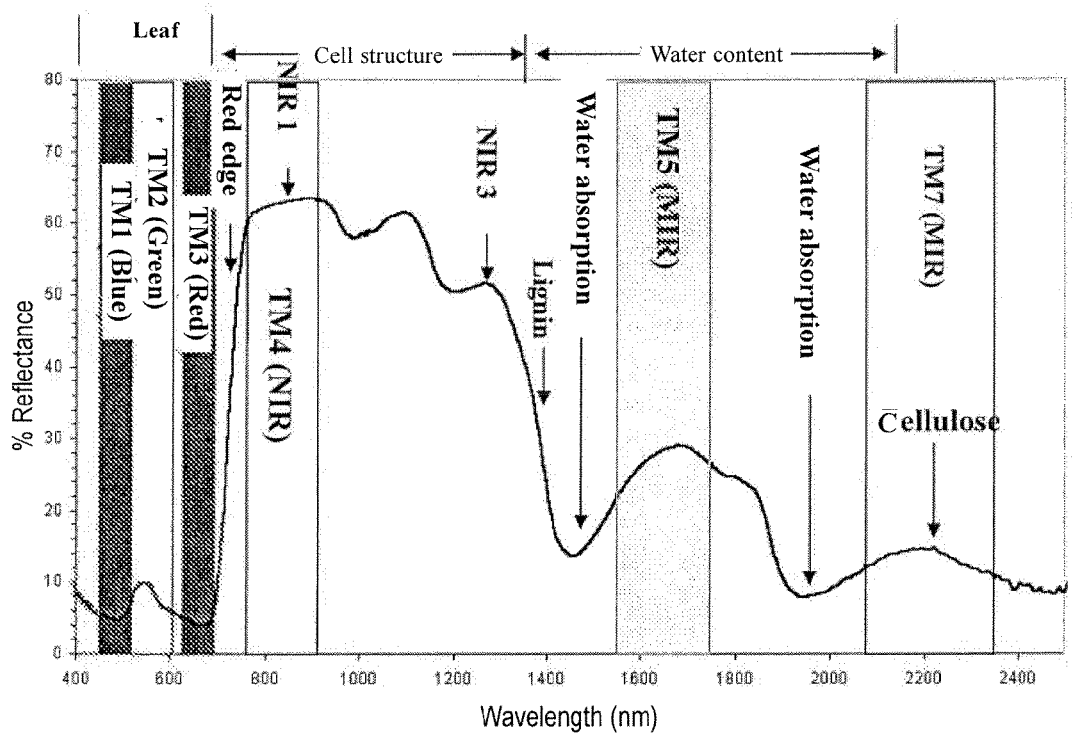
FIG. 3 is a schematic representation explaining the absorption/reflection characteristics of plants.
Figure 4:
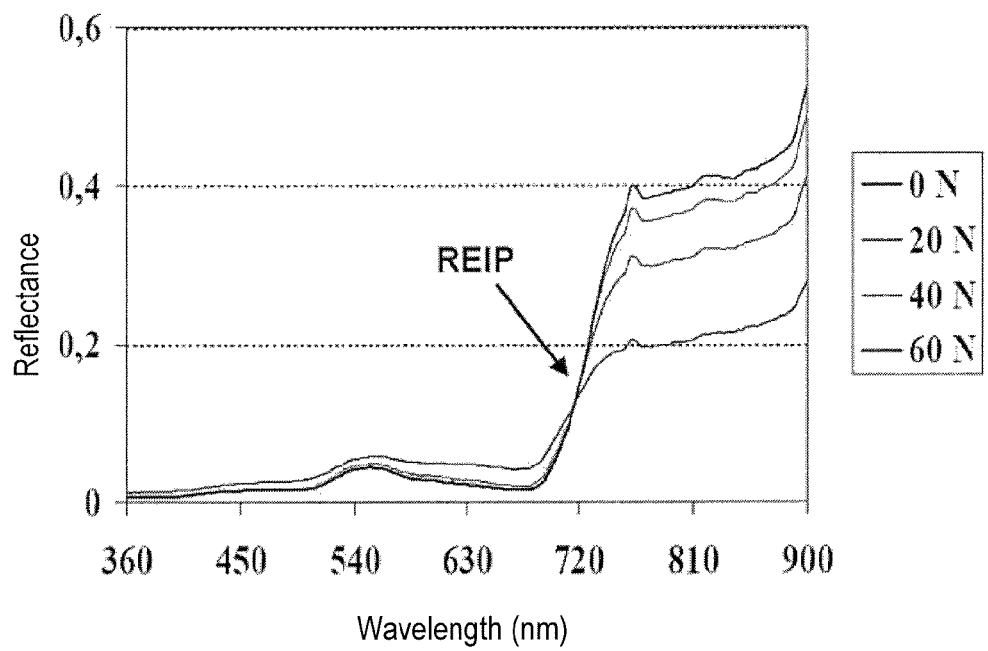
FIG. 4 shows the interrelation between the REIP and the nitrogen content of plants.

In accordance with FIG. 2, a set of two measuring devices in accordance with the to invention may be fastened to a tractor by way of example. The detected or calculated data is transmitted to the tractor via the Bluetooth connection of the interface 101. A wire connection into the tractor cockpit is not necessary. A PC on the tractor can carry out the evaluation of the data calculated in the sensor of the invention. To this end, the data is provided with GPS positions and, e.g., displayed on-line. Plant-growing is knowledge and yield maps are stored in the PC. A fertilizer distributor may thus be controlled by the PC in a suitable manner.

The invention claimed is:

1. A measuring device for determining a vegetation index value of plants, comprising a plurality of light emitting elements each of which emits substantially monochromatic light of a predetermined wavelength, a light receiving element which receives the light of the light emitting elements reflected by the plants and generates a signal indicating the respective intensity of the received light, and comprising a control means which successively drives the light emitting elements in a cyclical sequence, determines the respective intensity of the reflected light based on the output signal of the light receiving element, and calculates the vegetation index value, based on the determined intensities of the overall measuring cycle, characterized in that the light receiving element is a light frequency converter;

the light emitting elements include four light-emitting diodes each emitting a respective wavelength of 670 nm, 700 nm, 740 nm or 780 nm, wherein the half-width of the emitted light preferably is between 20 and 30 nm; and the control means calculates the red edge inflection point (REIP) as a vegetation index value in according with the following formula:

$$REIP = \lambda_2 + (\lambda_3 - \lambda_2)((P_1 + P_4)/2 - P_2)/(P_3 - P_2)$$

wherein the values $P_1$ to $P_4$ designate a respective measured intensity of the reflected light of the respective light-emitting diode, and $\lambda_2$ and $\lambda_3$ designate a respective wavelength of the respective light-emitting diode.

2. The measuring device according to claim 1, characterized by a current regulating means which controls the current supplied to each light emitting element and which is calibrated such that at a defined distance from a defined white surface each light emitting element generates the same output signal in the light frequency converter.

3. The measuring device according to claim 1, characterized in that the control means utilizes the REIP value as a measure for the nitrogen content of the measured plant.

4. The measuring device according to claim 3, characterized in that the control means supplies the respective determined nitrogen content to a mobile, preferably GPS-supported fertilization system, preferably via a Bluetooth interface.

5. A measuring device for determining a vegetation index value of plants, comprising a plurality of light emitting elements each of which emits substantially monochromatic light of a predetermined wavelength, a lighting means which emits light of several wavelengths, a light receiving element which receives the light of the light emitting elements reflected by the plants and generates a signal indicating the respective intensity of the received light, and comprising a control means which successively drives the light emitting elements in a cyclical sequence, determines the respective intensity of the reflected light based on the output signal of the light receiving element, and calculates the vegetation index value, based on the determined intensities of the overall measuring cycle, characterized in that the light receiving element is a light frequency converter; and the luminous power of the lighting means is controlled by the control means inversely proportionally to the ambient brightness.

6. The measuring device according to claim 5, characterized in that the lighting means is an incandescent lamp.

7. The measuring device according to claim 5, characterized in that the lighting means is oriented such that it illuminates at least the one area at which the light-emitting diodes are directed.

8. The measuring device according to claim 1, characterized by a further light-emitting diode which emits green light, wherein the control means determines the ratio of vegetation to soil surface area by subtracting its measurement value from the one of the light-emitting diode having the wavelength of 670 nm.

* * * * *